(12) United States Patent
Loetscher et al.

(10) Patent No.: US 8,894,854 B2
(45) Date of Patent: Nov. 25, 2014

(54) DIGESTER FOR HIGH SOLIDS WASTE

(75) Inventors: Lucas Hans Loetscher, Fort Collins, CO (US); Sybil Sharvelle, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 469 days.

(21) Appl. No.: 13/197,287

(22) Filed: Aug. 3, 2011

(65) Prior Publication Data

US 2012/0034681 A1 Feb. 9, 2012

Related U.S. Application Data

(60) Provisional application No. 61/370,159, filed on Aug. 3, 2010.

(51) Int. Cl.
| | |
|---|---|
| C02F 3/30 | (2006.01) |
| C12M 1/107 | (2006.01) |
| C12M 3/00 | (2006.01) |
| C12M 1/00 | (2006.01) |
| C12P 5/02 | (2006.01) |

(52) U.S. Cl.
CPC *C12M 21/04* (2013.01); *C02F 3/30* (2013.01); *C12M 23/44* (2013.01); *C12M 47/00* (2013.01); *C12P 5/023* (2013.01); *Y02E 50/343* (2013.01)
USPC ............ 210/603; 210/605; 210/622; 210/259

(58) Field of Classification Search
CPC ..... Y02E 50/343; C12M 21/04; C12M 47/00; C12M 23/44; C12P 5/023
USPC ......... 210/603, 605, 612, 613, 621, 622, 252, 210/259, 906
See application file for complete search history.

(56) References Cited

U.S. PATENT DOCUMENTS

| | | | |
|---|---|---|---|
| 4,396,402 A | 8/1983 | Ghosh | |
| 6,342,378 B1 * | 1/2002 | Zhang et al. | ................... 435/168 |
| 7,682,813 B1 | 3/2010 | Samani et al. | |
| 2002/0102673 A1 | 8/2002 | Zhang et al. | |
| 2007/0158264 A1 | 7/2007 | Zhang | |
| 2009/0206028 A1 * | 8/2009 | Jiang et al. | ................... 210/603 |
| 2009/0227003 A1 * | 9/2009 | Blotsky et al. | ............. 435/257.1 |

OTHER PUBLICATIONS

International Search Report, PCT/US2011/046416, Colorado State University Research Foundation, Apr. 9, 2012, 6 pages.
Kim, D. et al., Journal of Hazardous Materials, 2007, 146, pp. 81-85, Dec. 2, 2006.
International Preliminary Report on Patentability and Written Opinion of the International Searching Authority, PCT/US2011/046416, Colorado State University Research Foundation, Feb. 5, 2013, 8 pages.

* cited by examiner

*Primary Examiner* — Fred Prince
(74) *Attorney, Agent, or Firm* — HolzerIPLaw, PC

(57) ABSTRACT

A digester with separate stages for hydrolysis and methanogenesis is disclosed. The digester includes a leachate bay reactor, which may be configured as modular, multi-bay units. Waste material is added to the leachate bay reactor. A leachate storage tank is fluidically connected to the leachate bay reactor, which facilitates hydrolysis. Leachate from the leachate storage tank is recirculated through the leachate bay reactor. A high rate methanogenic reactor is fluidically connected to the leachate storage tank to cycle the leachate in a fixed film environment for biogas production from solubilized organic matter. The reactor may be operated in an anaerobic digestion mode, or a dual aerobic-anaerobic digestion mode. The reactor may also include a struvite system having a crystallizer unit and a separation unit to reduce ammonium and phosphate accumulation during operation.

18 Claims, 9 Drawing Sheets

DIGESTER FOR HIGH SOLIDS WASTE

CROSS-REFERENCE TO RELATED APPLICATIONS

The present application claims benefit of priority to U.S. Provisional Patent Application No. 61/370,159 entitled "Two-Stage Anaerobic Digester For Processing Of Animal Waste" and filed on Aug. 3, 2010, specifically incorporated by reference herein for all that it discloses or teaches.

GOVERNMENT RIGHTS

This invention was made with government support under Grant No. DE-FG26-07NT43196 awarded by the Department of Agriculture. The government has certain rights in the invention.

BACKGROUND

Bioenergy conversion (the conversion of biomass to useful energy) is gaining in popularity as the visibility of renewable energy increases. But growing crops specifically for bioenergy conversion raises separate concerns, such as competing with land and other resources used for growing crops for food and thereby increasing the cost of food. Therefore, using organic waste material instead, such as manure, crop residues, and organic municipal wastes, has become a more attractive alternative for use in bioenergy conversion.

Aerobic and anaerobic digestion of organic material are known processes for treating waste materials. Aerobic digestion, or "composting" as it is more commonly referred to, is the processing of waste materials in the presence of air. Aerobic digesters produce compost (a soil amendment) and heat. Anaerobic digesters process waste materials in the absence of oxygen, and produce a digestate suitable for use as a soil amendment or fertilizer. Anaerobic digesters are particularly attractive for treating waste materials, because the process reduces overall volume and mass of the waste while producing biogas used for heat and/or generating electricity.

In anaerobic digestion, microbes utilize the waste material as a food source, releasing nutrients (e.g., nitrogen and phosphorus) which are suitable for use as fertilizer. The microbes also produce a mixture of gases as a byproduct of the digestion process. This biogas is high in methane content, which has a high potential for generating energy.

Several anaerobic digestion technologies exist, including complete mix, plug flow, batch, fixed film, and anaerobic sludge blanket technologies. These technologies can treat waste materials having a total solids (TS) content of less than about 15%. Yet confined animal feeding operations (e.g., dairies and feedlots) produce large quantities of animal waste having total solids content much greater than 15%. Accordingly, this waste has to be diluted with large quantities of water before the waste can be treated using convention anaerobic digestion processes.

For purposes of illustration, 1000 metric tons of waste with 90% total solids needs to be diluted with 9000 cubic meters of water in order to be treated using a conventional complete mix digestion process. Using this much water in a waste treatment process is not desirable, particularly in arid western states where water comes at a premium. Even if this much water is available for use in waste treatment processes, dilution causes heavier inorganic particles (e.g., sand and soils) to settle in the digester. "Sandbars" may form at the bottom of the digester, which interrupt stable operation and necessitate frequent cleaning. In addition, having to pump such staggering quantities of water, and constructing a digester large enough to hold all of this water, renders these treatment processes difficult to implement in a cost effective manner.

Dry digestion technologies also exist. These technologies can operate with up to 35% total solids content, and thus reduce the amount of water needed to dilute the waste materials. For purposes of illustration, 1000 metric tons of waste with 90% total solids content only needs to be diluted with 2700 cubic meters of water. Compare this volume of water to the 9000 cubic meters of water needed for the complete mix digester example discussed above. But dry digestion processes are typically implemented as batch systems. The waste is loaded into a large reactor, moistened, and covered to maintain anaerobic conditions. This results in low hydrolysis rates and thus long retention times to be effective, which drives up the operating costs.

Leachate production with recirculation is a form of dry digestion. Leachate production processes are implemented by pumping liquid onto the surface of a bed of waste material so that the liquid percolates through the bed. As the leachate drains away from the solid, more leachate is added and/or recirculated onto the surface of the bed, so that there is a constantly exchanging film of leachate surrounding the waste material during the digestion process. However, the microbes (methanogens) used in anaerobic digestion processes are sensitive to low pH levels in the leachate bed. In addition, like other batch systems, the inoculum is completely exchanged at the end of each batch and the next batch takes time to re-grow an acclimated population of microorganisms before effective digestion can occur. Thus, leachate production processes generally exhibit low methane production efficiency.

SUMMARY

Implementations described and claimed herein address the foregoing problems by providing a digester and method of hydrolysis and methanogenesis in separate stages for digesting organic waste material. The digester may be operated in an anaerobic digestion mode, or in a dual mode with separate aerobic and anaerobic phases. In addition to biogas production, a soil amendment may be produced from the waste material remaining in the leachate bay reactor.

In an exemplary embodiment, a method of hydrolysis and methanogenesis in separate stages includes: recirculating leachate between a leachate bay reactor and a leachate storage tank; and cycling leachate from the leachate storage tank to a fixed film environment in a high rate reactor for methogenesis. During operation, water is absorbed into the waste material until saturation. The high rate reactor is also filled with water, and the water is recirculated through the leachate bay reactors.

In another exemplary embodiment, a digester is disclosed having separate stages for hydrolysis and methanogenesis. The digester includes a leachate bay reactor. The leachate bay reactor may be a multiple bay modular batch reactor. The leachate bay reactor facilitates hydrolysis. A leachate storage tank is fluidically connected to the leachate bay reactor to recirculate leachate through the leachate bay reactor. the leachate storage tank facilitates acido/acetogensis to compost the leachate. A high rate reactor is fluidically connected to the leachate storage tank to cycle the leachate in a fixed film environment provided by the high rate reactor for biogas production from solubilized organic matter.

In addition, the digester may also be implemented with a struvite system having a crystallizer unit and a separation unit. The struvite system reduces ammonium and phosphate accumulation during operation.

Other implementations are also described and recited herein.

BRIEF DESCRIPTIONS OF THE DRAWINGS

FIG. 2b illustrates an example flow pattern for the digester shown in FIG. 2a.

DETAILED DESCRIPTIONS

Figure 1:
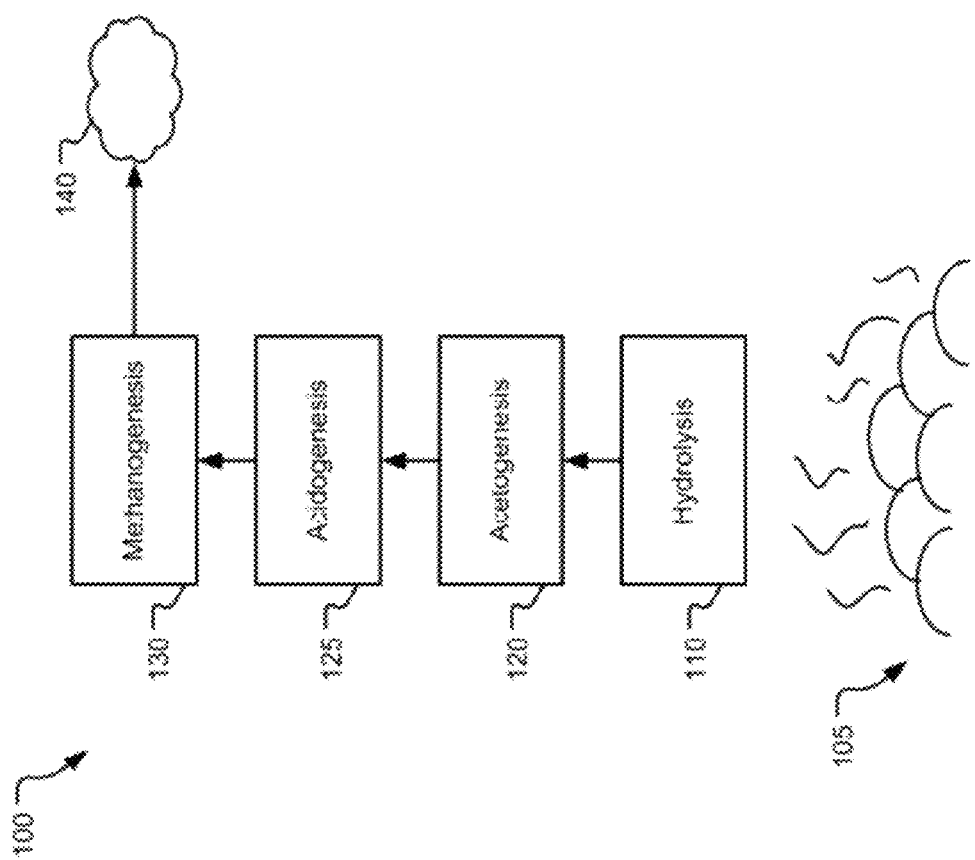
FIG. 1 illustrates an example biological process diagram.

The conversion of organic material into methane biogas is a multi-step biological process. FIG. 1 is an example high-level biological process diagram 100. The process includes providing an organic waste material 105, which undergoes the steps of hydrolysis 110, acidogenesis 120 and acetogenisis 125, and methanogenesis 130 which forms biogas 140. During hydrolysis 110, microorganisms release enzymes that biodegrade organic compounds, eventually rendering simpler and more soluble organic compounds. Hydrolysis 110 is often the key limiting step in anaerobic digestion of wastes containing solid materials. Following hydrolysis 110, soluble organic compounds rapidly undergo acidogenesis 120, and the compounds are converted into organic acids such as acetic, formic, and butyric acid. Acidogenesis 120 is followed by acetogenesis 125, which neutralizes these acids into compounds such as acetate, formate, and butyrate. Methanogenesis 130 uses the products from acetogenisis 125 to generate methane, a component of biogas 140.

The methane content of biogas 140 produced by anaerobic digestion can be as high as 70%, having an average energy of 750 BTU/ft$^3$. This ability to effectively stabilize the waste material 105, while releasing nutrients (useful as a fertilizer or soil amendment) and producing a combustible biogas 140 (useful to generate energy), makes anaerobic digestion an attractive process. Indeed, biogas 140 having high levels of methane is more readily utilized as an energy source other than biogases generated by other bioenergy conversion technologies, such as gasification or pyrolysis. The potential for energy generation during anaerobic digestion is also advantageous as compared to conventional aerobic waste stabilization processes. Indeed, anaerobic digestion is well accepted in the industry as a viable waste stabilization technology for both domestic and industrial wastewater treatment. However, not all anaerobic digesters are technically and/or economically feasible to implement on a large scale.

A plentiful source of high solids organic waste material is the waste product from confined animal feeding operations, which are particularly abundant across the arid western United States. Open dirt lots are often utilized where animals defecate onto the bare soil and the sun dries the manure. The dried manure is then removed with a box scraper. In cattle feeding operations, densities often exceed 50,000 cattle per square mile, and can generate upwards of 5 million pounds of dried sand/soil riddled waste every day. It is not feasible to dilute this quantity of waste with water for use with conventional anaerobic digesters. However, the digester described herein may be used to treat waste product such as this, and in the process, produce a digestate suitable for use as a fertilizer or soil amendment, while also producing a high-content methane biogas for use in heating and/or generating energy.

It is known that manure may have a very low hydraulic conductivity when used as a slurry. For purposes of illustration, manure slurries may have a hydraulic conductivities as low as 10 L/m$^2$/day. As excreted cattle manure is a viscous fluid which is composed of a suspension of small particles sizes which sort together creating low porosities and the associated low hydraulic conductivity values. As manure dries though these smaller suspended particulates agglomerate into larger particulates. These manure conglomerates have much higher hydraulic conductivity values. For purposes of illustration, some types of manure may have a hydraulic conductivity as high as about 1440 L/m$^2$/day.

To reduce the occurrence of, or altogether prevent issues related to poor hydraulic conductivity, multiple redundant methods may be implemented with the digester described herein to prevent substrate clogging and problems with buildup of inorganic materials. There are at least two methods, including facilitating conduction and reacting to reduced to reduced flow. There are multiple approaches to facilitate flow of leachate through waste and prevent hydraulic failure. Two methods include removing problematic waste portions from the waste stream, and/or diluting those portions with other substrates which impact positive characteristics. For multiple sourced wastes, careful consideration should be placed on the selection of suitable waste products. For example a dry lot dairy might generate a high solids dried manure in addition to a low solids (<5% TS) dairy parlor wash. The parlor wash may be excluded from the leachate bay reactor 210. Another example of removing problematic portions is the separation of fine particulates by screening the dried manure and removing a fraction of the smallest particulates. Both of these approaches generate a wasted fraction of material which can either be digested in the leachate storage tank 220, or composted with the post digested materials. Highly porous substrates can also be added to the waste to increase its porosity and hydraulic conductivity. These materials can either be organic or inorganic in origin. Organic substrates have the added benefit of contributing to the leachate's organic content through hydrolysis.

Figure 2A:
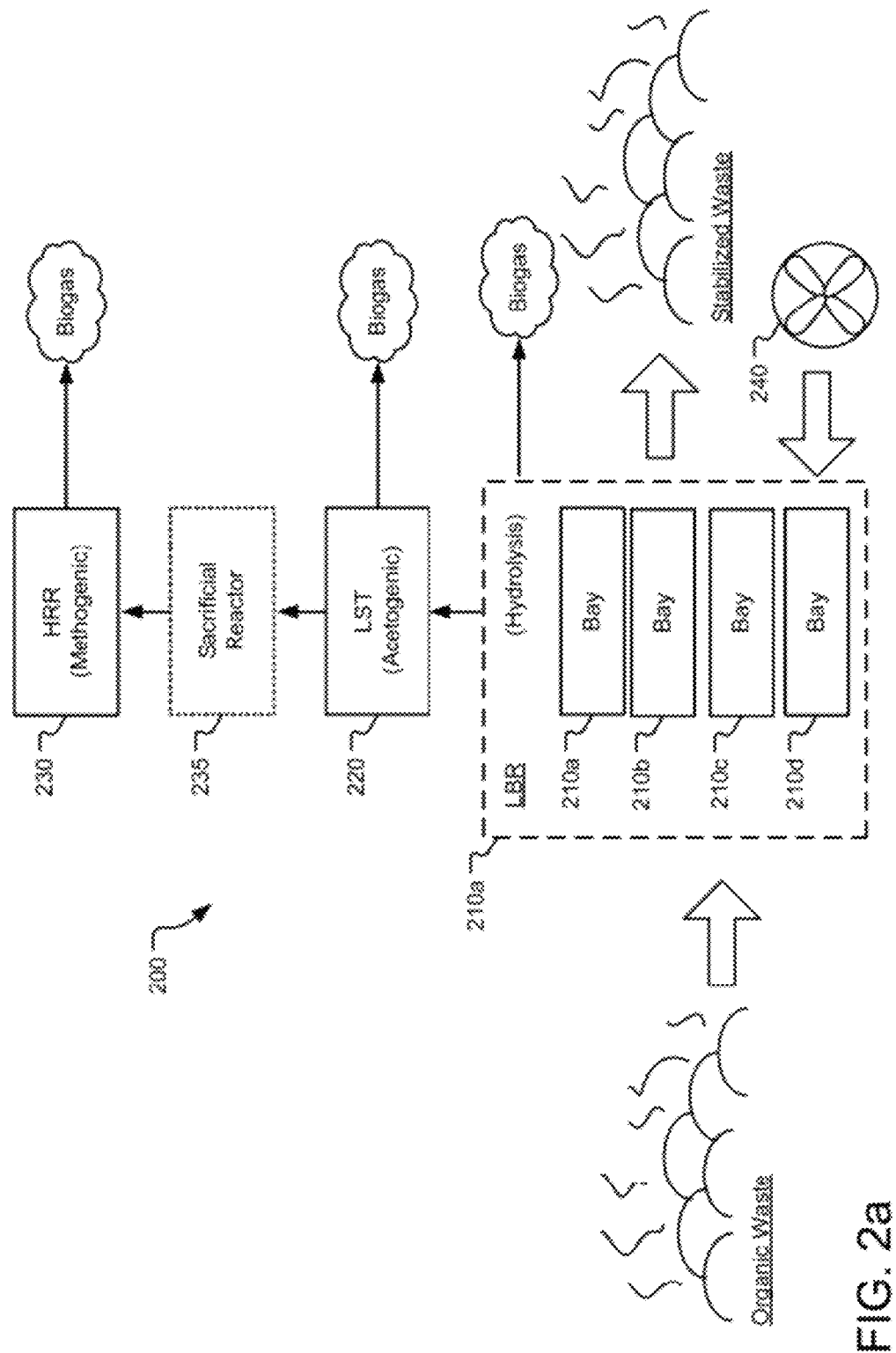
FIG. 2a illustrates an example multiple stage high solids digester.
Figure 2B:
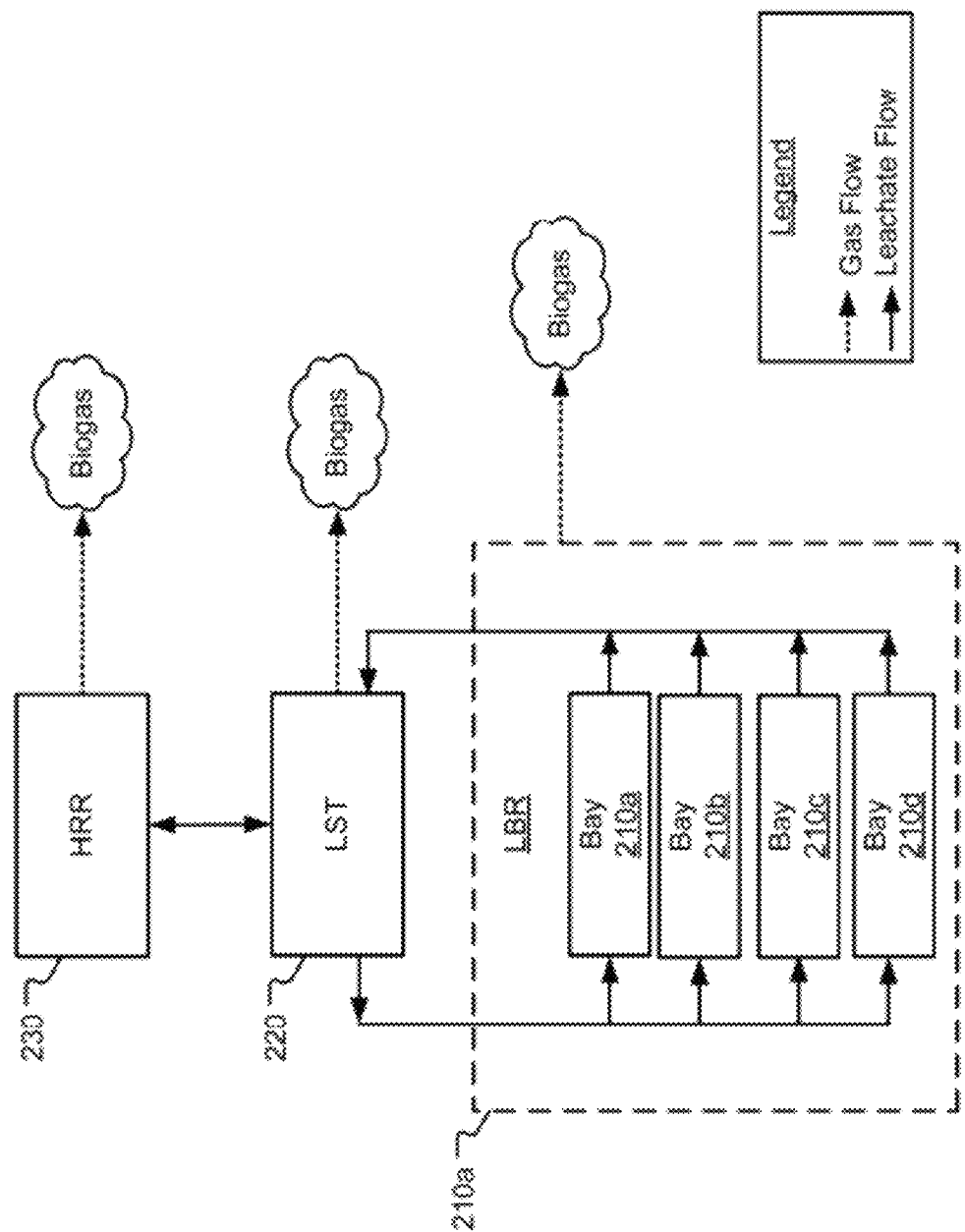

The other important step is to detect and prevent further deterioration of hydraulic conductivity once flow begins to slow. Logistical and material handling complications multiply as the waste becomes fully saturated. Therefore, the flow rate into the leachate bay reactor may be matched to the flow rate coming out of the reactor. Using this feed back mechanism the build up of water on top of the columns, and the subsequent formation of slurry conditions is reduced. FIG. 2a illustrates an example multiple stage high solids digester 200. FIG. 2b illustrates an example flow pattern for the digester 200 shown in FIG. 2a. In an example, the digester 200 enables methane generation from organic waste having more than 35% total solids content. In this design, the two most limiting stages of anaerobic digestion (hydrolysis and methanogenesis), are separated from one another. Separate reactors allow complete optimization for each stage. Leachate recirculation is used in the first stage of the digester, which operates as a modular batch type reactor. The second stage is a compositing tank for the leachate. The final stage (methanogenesis) occurs in a fixed film environment.

In an example, the digester 200 has a leachate bay reactor (LBR) 210. The leachate bay reactor 210 may include one or a plurality of individual leachate bay reactors 210a-d. Organic waste material may be provided into the leachate bay reactor along with water, and allowed to digest, in one example, for 10-30 days. A leachate storage tank (LST) 220 is fluidically connected to the leachate bay reactor 210 to recirculate leachate through the leachate bay reactor 210 during the digestion process. A high rate reactor (HRR) 230 is fluidically connected to the leachate storage tank 220 to cycle the leachate in a fixed film environment for biogas production. The high rate reactor 230 is used for biogas production using a low solids leachate (from the leachate storage tank 220). It is noted, however, that biogas may be generated in any or all of the reactors. Biogas may be generated on a continuous basis, e.g., after digestion begins. Following the digestion process, the stabilized waste material may be removed from the leachate bay reactors and composted. The composed waste material may be suitable for use as a soil amendment (e.g., fertilizer).

Providing a separate leachate bay reactor 210 enables better process control. After an initial startup period, where water is absorbed into the waste material, an equilibrium condition is established such that flow rates out of the leachate bay reactor 210 is nearly equal to flow rates into the leachate bay reactor 210. If clogging occurs (e.g., liquid retention in the leachate bay reactor 210), the flow rate out of the leachate bay reactor 210 is lower than the flow into the leachate bay reactor 210. At this point, the pumps can adjust flow to reduce or altogether prevent agglomeration of the manure and associated reductions in flow.

Providing a separate leachate storage tank 220 servers to reduce or eliminate exposure of chemical toxicity to methanogenic organisms in the digester portion of the reactor. Acidic methanogenic toxicity is a common failure issue related to digestion systems. This is commonly caused by an accumulation of organic acids, and is commonly corrected through the addition of caustic. However, separating the leachate storage tank 220 from the high rate reactor 230 allows process control over pH levels in the high rate reactor 230. In an example, an acidic leachate may be slowly fed into the high rate reactor 230 allowing time for the completion of the de-ionization of the organic acids and the subsequent stabilization of pH. This serves maintain the pH near the range of 8-8.5 while reducing the amount of caustic.

As methanogens often clog conventional leachate-based digesters before the completion of digestion, it may be desirable to prevent methanogenic growth in the leachate bay reactor 210. Growth of methanogenic organisms in the leachate bay reactor 210 is limited by high rate reactor 230 through increased competition for nutrients. The high rate reactor 230 is better optimized for growth of methanogens, e.g., as compared to the leachate bay reactor 210. In addition, acidic conditions in the leachate storage tank 220 limit growth of methanogenic organisms in the leachate before water is reapplied on the top of the leachate bay reactor 210.

Within leachate bay reactor 210 conditions are maintained to facilitate the growth of hydrolyzing bacteria. To speed the establishment of these bacteria it is advantageous to increase the initial concentration of bacteria. This can be accomplished through leachate inoculation, or substrate inoculation. A possible method of leachate inoculation is to saturate a freshly filled leachate bay reactor 210 with leachate from a mature leachate bay reactor, thereby transferring organisms suspended in the leachate. The second method mixes substrate from a mature leachate bay reactor 210 into the fresh substrate as it is placed into the bay.

Anaerobic conditions are maintained in the leachate bay reactor, where hydrolysis occurs in the leachate bay reactors, operated in batch. When maximum anaerobic sollubilization of solid organic material to the liquid phase is achieved, batch anaerobic operation is terminated. The remaining recalcitrant solid material is then composted under aerobic conditions, which helps to stabilize the waste and control the release of odorous compounds. An aerobic environment can be achieved through forced aeration within the system or through the transference of substrate to an external composting system. In either composting configuration, liquid or solid additives can be utilized to promote more complete substrate degradation and/or higher temperatures for further pathogen reduction. Aerobic inoculum (e.g., in the form of mature compost or aerobic leachate) can be added to reintroduce aerobic organisms. Additional carbon sources (preferably recalcitrant lignocellosic wastes to prevent competition with digestion feedstocks) may also be incorporated to ensure sufficient energy for microbial growth. Liquid is no longer recirculated through leachate bays during aerobic mode operation.

Digestion of highly recalcitrant wastes may be facilitated by following the anaerobic/aerobic cycle with a further anaerobic cycle. In this configuration the fast growing aerobic organisms (e.g., bacteria and fungi) have access to a wider array of organic molecules than anaerobic bacteria. The energy garnered by the aerobic organisms is converted to biomass which is readily biodegraded by the anaerobic organisms at the onset of the subsequent anerobic cycle. This process may continue cycling until the wastes are effectively stabilized. Innoculation may be repeated.

All liquid from the leachate bay reactors is delivered to the storage tanks, where effluent from the anaerobic digester is also collected. Combining effluent from the anaerobic digester with effluent from the leachate bays results in dilution of acids produced through the leachate bay reactors, thus improving process efficiency for hydrolysis in the leachate bay reactors. The process components and methods described herein can be implemented as a total co-digestion system, in which solids are treated in the leachate bay, and slurries in the leachate storage tank and solutions can be directly injected into the fixed film reactors.

The digester 200 is not limited to any particular configuration. Indeed, the modular nature of the digester 200 (i.e., having separate reactors) enables a wide variety of implementations. Different implementations may provide different levels of process control. For purposes of illustration, a "sacrificial" high rate reactor 235 may be placed in the front of the high rate reactor 230. When gas production from the sacrificial reactor 235 drops (indicating a process upset), leachate flow can be slowed into the main reactor 230. These, and other implementations, will be readily understood by those having ordinary skill in the art after becoming familiar with the fundamental teachings set forth herein.

The digester may be sized based on any number of design considerations. In an example, each leachate bay reactor 210 may be sized based at least in part on whether or not transportation is desired, and scale of project. Because the leachate bay reactor 210 may be modular in nature, the number of modular reactors 210a-d may be based at least in part on the desired retention time. Also in an example, the leachate storage tank 220 may be sufficient in size to hold a drain volume from the leachate bay reactor 210 when pumped at the highest conduction rate (e.g., about 1 $L/m^2/min$). The high rate reactor 230 may be sized according to the ability to treat leachate based on kinetics of biodegradation of organic acids.

As cattle manure is deposited and dried within the outdoor confinement pens its methane potential per unit of solids mass decreases. Yet due to the evaporation of water the methane production per unit of total mass increases slightly. Due to increased methane production and the improved material handling provided by the solid nature of the manure, there is increased potential for transporting manure to a regional leachate bay digester system. The proposed configuration with its modular sequential batch mode operation lends itself well to such a regional digestion system. As an example of this, wastes may be collected in a transportable leachate bay 210 which is transferred from the generation site to the digester site where it is placed in a heated enclosure. The bay may be sealed and plumbed to allow for the leachate flow under anaerobic conditions. At the conclusion of the anaerobic phase the waste may be composted directly in the bay, after which the bay can be transported to the wastes final destination and emptied.

Operating conditions may be based on any number of design considerations. To increase solution transport, the flow rate through the leach bay reactor 210 may be selected to be as high as feasible. In an example, a flow rate of about 1 $L/m^2/min$ was determined as a reasonable rate for many waste materials. The flow rate can be achieved, maintained, and adjusted, by recirculating water.

In general, effective operating temperatures may be between about 32-37° C. (mesophilic conditions), or between about 45-50° C. (thermophilic conditions). The operating temperature may depend on design considerations and is not limited to these examples. It is also noted other design parameters may also affect operating temperature. For example, under mesophilic conditions (e.g., about 35° C.), a 24 h retention time in the high rate reactor 230 may not be sufficient for complete biodegradation. Therefore, longer retention times may be used when operating with single pass leachate treatment.

The operating pH also may depend at least to some extent on design considerations and desired function. In an example, the leachate bay reactor 210 and the leachate storage tank 220 are maintained at a lower pH. For purposes of illustration, an effective pH level is less than 7 (e.g., about 6). The pH level of the fixed film environment may be maintained at higher pH levels. The pH will depend at least to some extent on the desired methanogens used for digestion. Typically the pH level of the fixed film environment may be maintained between about 6.8 and 7.2, or between about 7.5 and 8.5. Generally, a pH of 8 is desired for the high rate reactor 230.

During operation, hydrolysis occurs in the multiple bays 210a-d of the leachate bay reactor 210. The leachate is recycled through the leachate storage tank 220 for compositing. The leachate storage tank 220 provides a location to facilitate the acido/acetogenesis. The leachate storage tank 220 also serves as a microbial inoculum reservoir. The leachate is then cycled through the high rate reactor 230, which operates as a high rate fixed film reactor where high-content methane biogas is produced from the solubilized organic material in the leachate.

Although the digester 200 incorporates aspects of dry digestion and leachate production, the multi-stage design enables the digester 200 to be used for processing a wide variety of waste materials. For example, diluted waste streams with mid-range solids (e.g., about 1-10% total solids content) can be fed into the leachate storage tank 220, while the more soluble industrial wastes with low solids (e.g., greater than about 1% total solids content) can be fed directly into the high rate reactor 230. Accordingly, the leachate storage tank 220 acts as a sludge blanket reactor producing a clear supernatant which can be fed into a high rate digester 230.

It is noted that the digester 200 can be filled with waste material on an irregular basis. As such, operation of the digester 200 does not depend on major changes in current management practices. Capital costs can potentially be reduced because the reactor tanks do not need to be built to hold large quantities of dilution water used by conventional technologies. Retention times in the leachate bay reactor 210 are reduced compared to retention time for other dry digestion methods. In addition, this design results in an overall lower digester footprint, and provides for flexible setup of the digester 200.

It is also noted that inorganic materials (e.g., sand and soil mixed in with the organic waste material to be digested), do not cause operational upsets. Inorganic material remains in the leachate bay reactor 210 during digestion, and does not enter the leachate that is ultimately digested in the high rate reactor 230. Upon termination of a batch, remaining solid waste material can simply be dumped out of the leach bay reactor 210 and land applied or composted further.

In addition, the digester 210 is suitable for use with a wide variety of waste material. But regardless of the type of waste material being treated, the waste material should conduct water. Testing has shown a variety of waste material can conduct water with at least 1 $L/m^2/min$ based on the following mixture percentages by volume displaced in manure. In the following examples, (1) dry lot collected dairy manure conducted water for about 16 days; (2) horse manure conducted water for about 35 days; (3) a 50% dairy and 50% horse manure mixture conducted water for about 35 days; (4) horse manure conducted water for about 35 days; (5) a 75% dairy manure and 25% waste hay mixture conducted water for about 21 days; (6) a 75% pulverized feedlot manure and 25% waste hay mixture conducted water for about 21 days; (7) a 75% pulverized feedlot manure and 25% waste hay mixture conducted water for about 21 days. These waste materials are provided only for purposes of illustration and are not intended to be limiting. Other waste materials which may be suitable for use with the digester include, but are not limited to, urban biomass (including grass clippings and tree leaves), agricultural biomass (including corn stalks and waste straw), and kitchen waste.

The water used to dilute the waste material can be categorized according to use and recyclability. A first category is the water absorbed into the waste material until the waste material becomes saturated. This water is generally not recycled during operation. Another category is the water which drains from the leachate bay reactors 210 and is stored in the leachate storage tank 220. This water is generally recyclable during operation. Another category is the water used to fill the high rate reactor 230. This water is also generally recyclable during operation.

Water may be recycled by recirculation through the digester 200, for example, as depicted in FIG. 2. Recirculating the water conserves large quantities of water, particularly in comparison to conventional technologies. In an example, extra supply water may be used to dilute the leachate after concentrations of about 3000 mg/L ammonia/nitrogen are exceeded. In another example, an ammonia removal technology may be used under these conditions instead, such as ammonia stripping or the struvite precipitation process described below.

Before continuing, it is noted that the example implementation of the digester 200 described above with reference to FIGS. 2a-c is merely illustrative. Numerous additional aspects and other configurations are also contemplated as being within the scope of the claims.

For purposes of illustration, further example implementations may be directed to waste collection. The most common method for collecting dry manure at dairies and feedlots in the arid west is with a box scraper. The box scraper is towed behind tractors to pulverize compacted manure while minimize soil gouging. However, the box scraper is ineffective at collecting manure slurries. During wet periods, an established waste management practice is to use fibrous bedding products, such as wheat, straw, and corn stalks, to facilitate manure collection. Addition of these materials still results in a waste product capable of being processed in the leachate bay reactor 210, without imposing hydraulic conductivity limitations. It is noted that the leachate bay reactor 210 is particularly well suited to further serve as a transporting container for the wastes collected from a region.

In addition to collection, automated feed and removal mechanisms may be implemented with the digester 200 to reduce labor input. Automating mechanisms, such as augers, conveyors, and automated scrape methods, to name only a few examples, may be utilized to facilitate waste handling.

With regard to operational parameters, it is understood that thermophilic conditions improve hydrolysis rates and increase total gas production. Such conditions may be readily provided in the digester 200 with additional heating. In an example, this heat may be produced using the biogas generated during the digestion process. Indeed, the increased gas production which results under thermophilic conditions may be sufficient in itself to produces ample heat through cogeneration to provide thermophilic conditions.

Controlled oxidation/reduction processes may also be employed for composting solids. Anaerobic bioconversion pathways produce methane, but are ineffective at breaking down compounds such as lignin and hemicelluloses. Aerobic pathways, although inhibiting bioenergy generation, are very efficient at degrading recalcitrant compounds. But both pathways may be utilized in the digester 200 to provide various benefits. For example, anaerobic digestion may be utilized for the most biodegradable compounds, and then processing may switch to aerobic conditions to degrade recalcitrant compounds in the water material. Then processing may switch back again to anaerobic conditions such that the previously indigestible constituents are indirectly converted to methane. Such a process may be used to better stabilize the wastes while still producing biogas.

In an example, these "dual" aerobic and anaerobic phases may be accomplished using one or more blower 240 to pump air through the under drain in the leachate bay reactor 210. Indeed, the blower(s) 240 may be methane powered blowers. Operating the blowers 240 creates an efficient composting system aerobically stabilize the waste material. The blowers 240 may also serve to dry the waste material, facilitating mechanical removal of the dried and stabilized compost. The blowers 240 are simply turned off to return the digester 200 to an anaerobic environment.

In the combined or dual process, waste materials are repetitively processed through the leachate bay reactor 210. Aerobic organisms which accumulate in the composting process are hydrolyzed along with new manure in the leachate bay reactor 210 to further increase the organic content of the leachate. Continual composting and digestion cycles eventually produce a less useful quality leachate, and the digester 200 may need to be restarted with fresh waste products.

The under drain can be manifested in a multitude of configurations. Examples include the utilization of rigid screens, porous loose materials, organic, inorganic, or synthetic composition are all possible incarnations of this portion of the leachate bay reactor 210. In addition to producing biogas, the digester 200 may also be used for nutrient recovery. The production of biogas is controlled by bacteria and achaea organisms. These organisms, known as methanogens, produce methane as a metabolic byproduct in anaerobic environments. Methanogens are sensitive to high ammonium concentrations, which may present in manure leachate. In addition, anaerobic digester liquor may be applied to cropland as a fertilizer. But typical concentrations of phosphate in the liquor can overwhelm the land, causing excess phosphate to run off into lakes and rivers, leading to eutrophication and destruction of native ecosystems.

One technique to prevent ammonium levels from becoming cytotoxic is to sparge the ammonia out of the leachate and capture it either biologically or chemically. Biological absorption is advantageous because the ammonia containing gaseous streams are entrained into the air used to aerate the bays going through an aerobic phase of operation. Here biological uptake returns nitrogen to the waste itself where the nitrogen can be used to as a soil amendment Ammonia stripping does not remove phosphorus which is another valuable fertilizer. Chemical or biological phosphorus absorption technologies may be employed to remove the phosphorus directly from the leachate, either by mixing solid absorbents into the waste substrate or including a separate reactor.

Another method which reduces both phosphourus and ammonia is contents, is by crystallization as a mineral called struvite. Crystalline struvite has a stoichiometric ratio of one, and thus is a viable candidate for reducing ammonium concentrations below toxic levels. At the same time, crystalline struvite also removes phosphate (as orthophosphate) from the leachate. Struvite can be applied to fields as a slow release fertilizer, and is currently valued at $320/ton. As such, a novel struvite precipitation system is disclosed herein as it may be implemented with the digester.

Struvite, $Mg(NH_4)(PO_4) \cdot 6H_2O$, is formed according to the following reaction:

$$Mg^{2+} + NH^{4+} + PO_4^{3-} + 6H_2O \leftrightarrow Mg(NH_4)(PO_4) \cdot 6H_2O$$

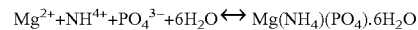

Manure leachate (on its own) typically does not contain the proper amount of Mg needed to form struvite. Accordingly, $Mg(OH)_2$ and $MgCl_2$ can be added to the feedstock such that the Mg:P ratio is close to 1.

Struvite has a solubility product $K_{sp} = [Mg^{2+}][NH_4^+][PO_4^{3-}]$, which if exceeded, precipitates solids from solution. The optimal pH levels for struvite formation is in the range of about 8.5-8.7. Because the ammonia/ammonium equilibrium is pH dependent, the ammonium concentration decreases significantly above a pH level of 9, reducing the $K_{sp}$ value, and ultimately reducing the precipitation of struvite. At struvite's optimal formation pH of about 8.5-8.7, an ammonium concentration of approximately 1500 mg/L can significantly alter the production rate of methanogens. The pH can be monitored with a pH probe and regulated with KOH, NaOH, and $CaCO_3$.

Previous struvite generators have used membranes, fluidized beds, and crystallizing technology, such as settling tanks, batch reactors, and continuously stirred tanks. However, the many fines that are produced upon supersaturation cause recovery issues when used in digestion processes.

Figure 3B:
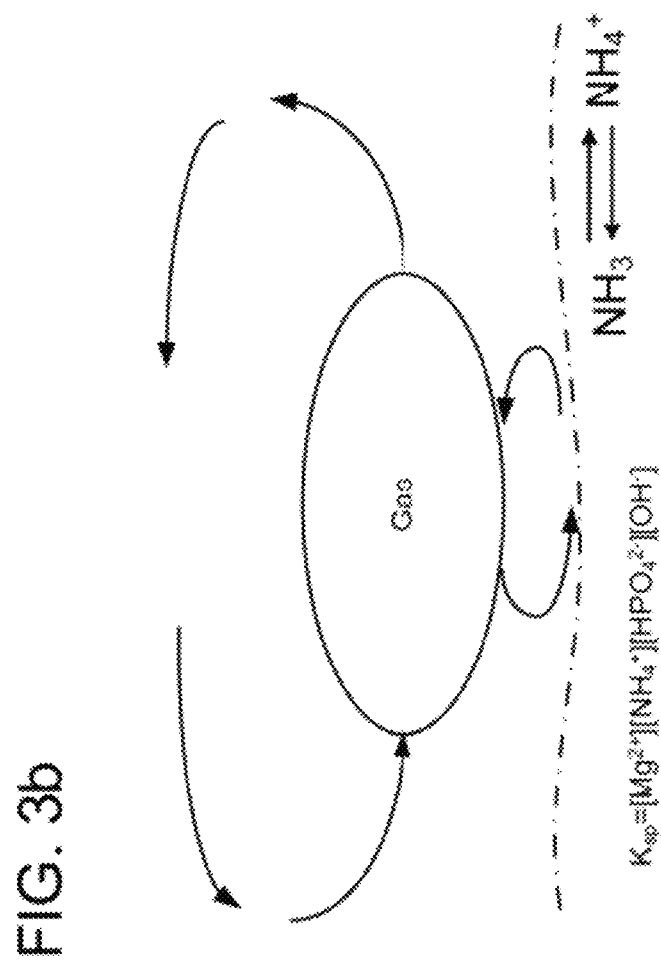
FIG. 3b illustrates an example sheering force of gas on liquid.
Figure 3A:
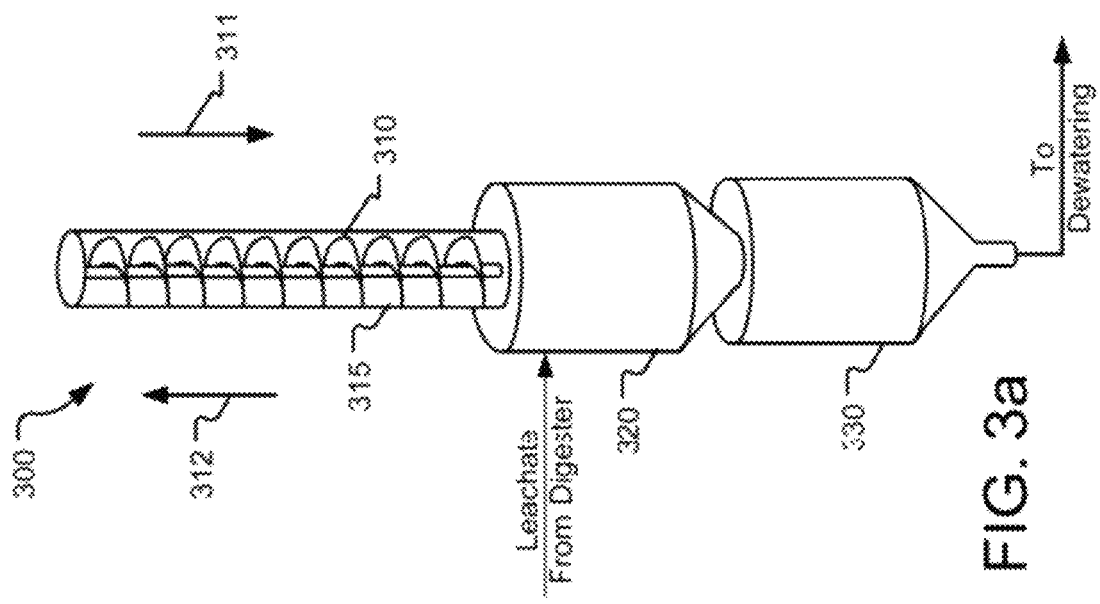
FIG. 3a illustrates an example three stage crystallizer.

FIG. 3a illustrates an example three stage crystallizer 300 having an auger assembly 310, hydrocyclone classifier 320, and gravity settling basin 330. The crystallizer combines the functions of producing struvite and then separating the struvite (and hence ammonium and phosphate) from the leachate. The auger assembly 310 is used to compartmentalize the column 315 into a series of continuous stirred tank reactors (CSTRs) to increase the residence time of crystal fines, and yielding larger crystals. In an example the auger assembly 310 transforms a three foot vertical height column 315 into a ten foot path-length for crystal formation. The auger 310 also provides a desirable solids retention time for the crystallization process.

Separation in the auger assembly 310 may be further improved using a controlled up-flow of gas. In an example, the gas is directed to travel from the bottom of the auger to create mixing by the sheering force of gas on liquid, as illustrated in FIG. 3b. That is, the liquid phase may spiral down the auger assembly 310 (as illustrated by arrow 311), while the suspended fines are encouraged to travel up the auger (as illustrated by arrow 312) by the countercurrent gas flow. This countercurrent gas flow serves to strip ammonia from leachate in the lower portions of the auger assembly 310, shifting the equilibrium away from precipitation. Further up the auger assembly 310, the saturated gas diffuses ammonia into solution to shift the equilibrium back towards ammonium, creating precipitation. At steady state, the headspace gas is saturated with ammonia, and a concentration gradient of ammonium exists in the auger assembly 310. The concentration is greatest near the top phase boundary and bottom gas feed port, decreasing as the center of the auger assembly 310 is reached. Accordingly, the crystallization can be controlled to some extent by adjusting the gas flow rate, and thus purging ammonium and phosphate from the leachate can be controlled by the digester operator.

Also during operation, larger crystals of struvite (along with some fines) travel below the auger assembly 310 to the hydrocyclone-like separation unit 320 where manure leachate is fed tangentially into a tank to form a weak vortex. The vortex causes heavier particles to travel closer to its axis of rotation, and light/small particles travel toward the outside. An outlet port positioned on the wall of the vessel takes advantage of the particle size separation, and feeds the smaller separated crystals back to the auger assembly 310 so that the small fines have a better opportunity to be further suspended for growth (secondary nucleation).

Crystals that travel to the bottom of the hydrocyclone classifier 320 continue to the last separation unit and into the settling tank 330, where crystal free leachate can be removed. Large crystals may be fed to the settling tank 330, as the previous separation units have caused sufficient growth of the crystals to the point where the crystals settle more quickly than the original fines. After the solids reach the bottom of the settling tank 330, slurry may be drawn out through a valve, and proceed to a dewatering process. The liquid in the vessel may be continually drawn out at a low flow rate to complete the continuous process and prevent accumulation from a continuous feedstock. Accordingly, the crystallizer 300 may be operated as a continuous system.

It is noted that the example implementation of the crystallizer 300 described above with reference to the drawings is merely illustrative. Numerous additional aspects and other configurations are also contemplated as being within the scope of the claims.

In another example, aerobic leachate can be sprayed on the waste material to facilitate growth of thermophilic/mesophilic aerobic organisms. Excess ammonia stripped from the top of a crystallizer 300 can be blown on the waste material, along with air. The ammonia is subsequently absorbed by organisms to create a nutrient-dense fertilizer/soil amendment.

EXAMPLE

Figure 4:
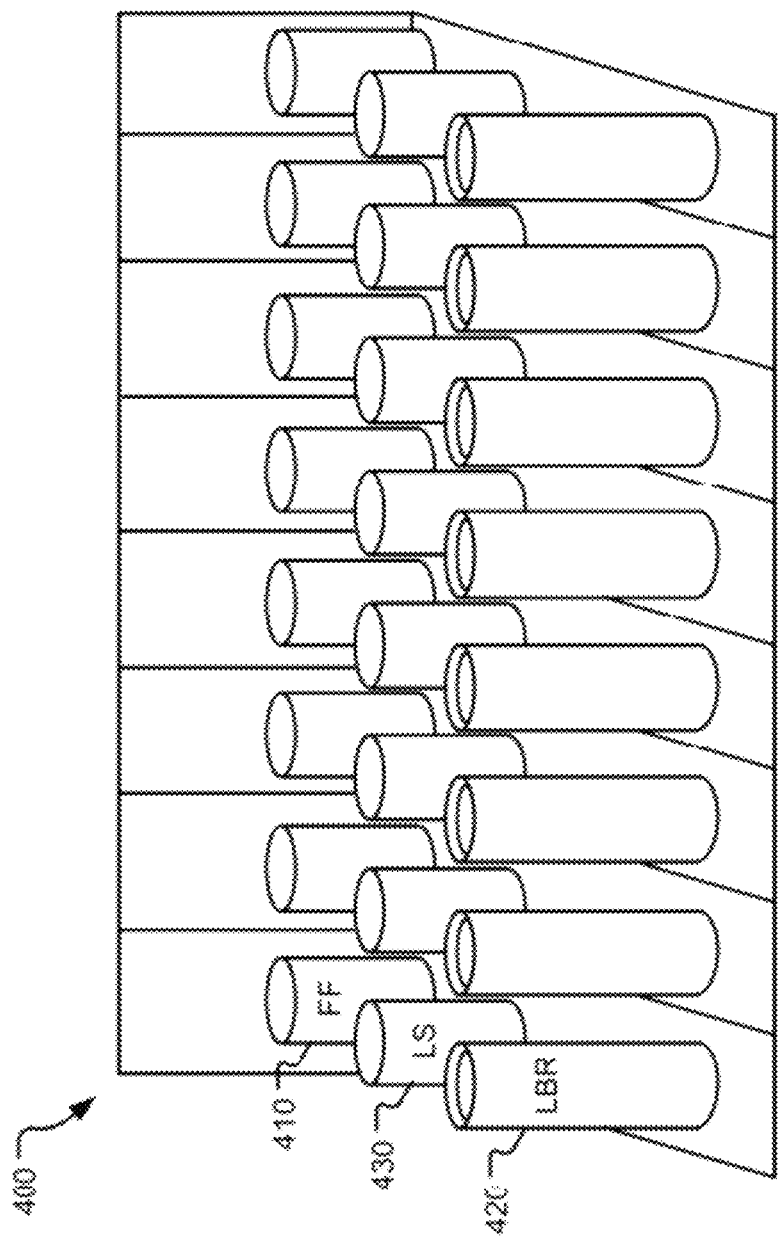
FIG. 4 illustrates an example reactor array.

A bench scale test was performed which operated at mesophilic conditions for three weeks. FIG. 4 illustrates an example reactor array 400. In this example, fixed film reactors 410 were utilized to simulate the digester high rate reactors for methane generation. The leachate bay reactors 420 were constructed using a 3 inch diameter PVC pipes contained within a larger 4 inch polycarbonate enclosures. The leachate storage tanks 430 and the fixed film reactors 410 were modeled using 3 inch diameter PVC pipes. The fixed film reactors 410 were then filled with 0.25 inch diameter plastic spherical pellets with a density slightly higher than water, to provide fluidization.

In this example, one liter aliquots of waste were compacted into a 900 mL leachate bay reactors 420, two liters of reverse osmosis (RO) laboratory grade water was added to the leachate storage tanks 430, and one liter of aged leachate water was added to the fixed film reactors 410 for initiation of bench scale tests. The flow rate was set at 0.66 ml/min into the leachate bay reactors 420. Leachate from the leachate storage tank was pumped at a flow rate of 0.33 ml/min to the high rate reactor, resulting in a retention time of about 24 hours. The leachate was completely recycled through the leachate storage tank during a 321 day test duration.

Figure 5:
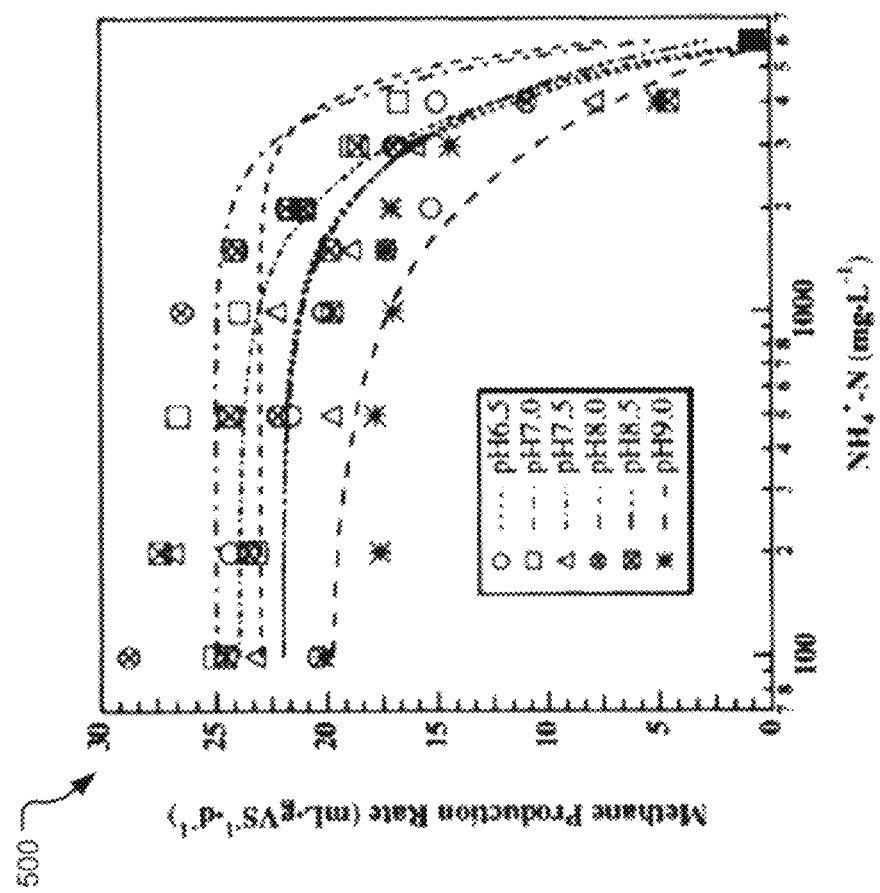
FIG. 5 is a plot of actual example data showing the relationship between methane production rate and ammonium-nitrogen concentrations at various pH levels.

The following manure mixtures were tested: (1) 50% horse manure and 50% dairy manure, (2) 25% straw and 75% dairy manure, (3) 50% straw and 50% dairy manure, and (4) 25% straw and 75% feedlot manure. Results of the testing are shown in FIG. 5. FIG. 5 is a plot of example data 500 showing the relationship between methane production rate and ammonium-nitrogen concentrations at various pH levels. The flow rate to the leachate bay reactors 420 prevented manure agglomeration, and the subsequent loss of hydraulic conductivity which would otherwise be expected.

The systems and methods described herein provide substrate flexibility. Dry solid wastes that have historically been underutilized in the digestion industry (such as solid dried manures, agricultural biomass including crop residue, and organic municipal solid waste) are good candidates for utilization within the leachate bay reactor. Methods to pretreat and/or handle manure in the leachate bay reactor may be implemented to improve liquid flow through the system, and thus process performance. Substrates which exhibit low hydraulic conductivity can be combined with other waste products to increase the conductivity and overall reaction rate of the waste product. An example technique is to mix these low porosity/low wet shear strength wastes (related to air void volume and the tendency for these to collapse under weight) with wastes with high porosity and high wet shear strength. The digestion rates of both substrates may be increased in such a configuration. Thus the entire space is used as an improved digestion space by increasing hydrolysis reaction rates as well as recovery of leachate to be used in the further stages of the process.

Figure 6:
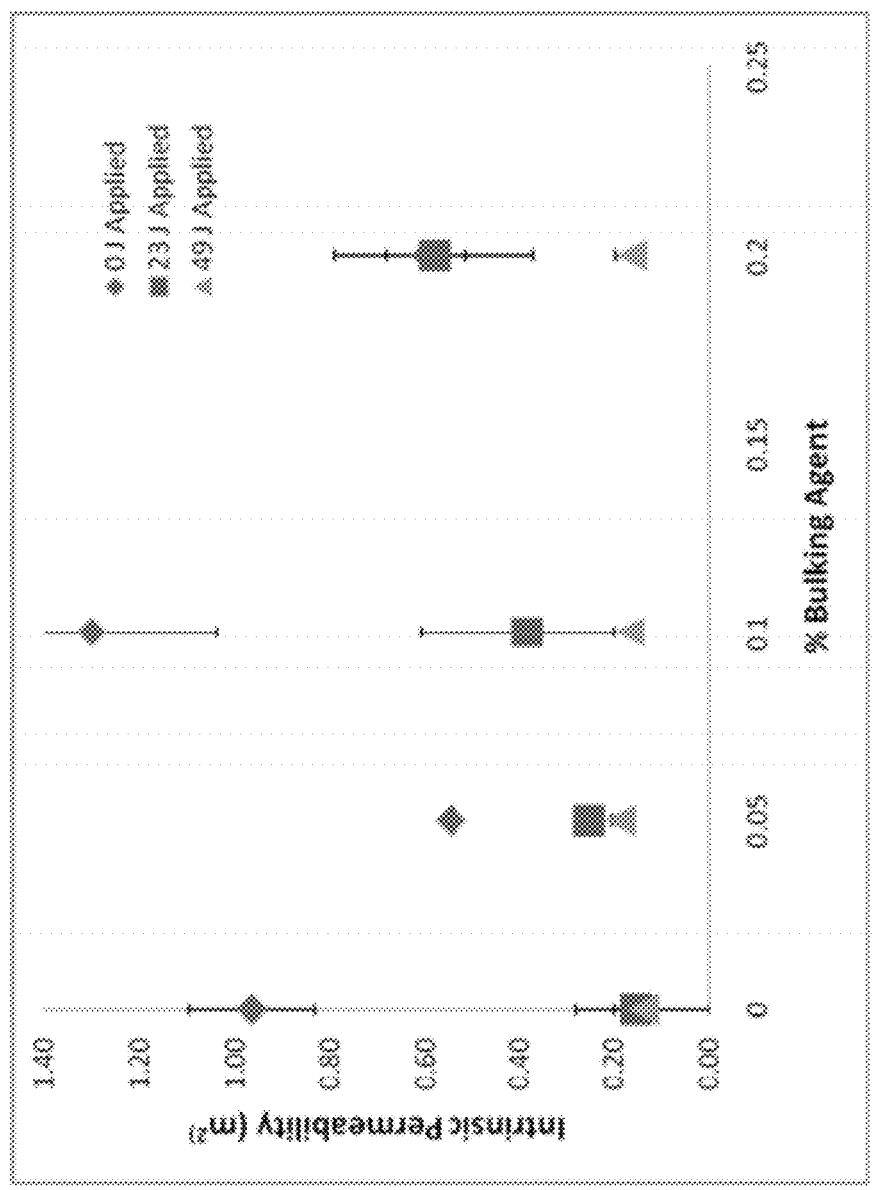
FIG. 6 shows the effect of straw and compression on intrinsic permeability in feed lot waste.

FIG. 6 shows the improvement of manure sample permeability due to addition of low percentages by weight of wheat straw at various compressions. Even when 23 J of energy were applied to the waste material, increasing permeability was observed with increasing addition of straw material. This demonstrates that addition of the straw can improve permeability when the waste material is under compression, which would be the case in leachate bay reactors in a full scale system. While this trend is not observed when 49 J are applied, this data demonstrates the benefit of straw addition to improve waste permeability.

Figure 7:
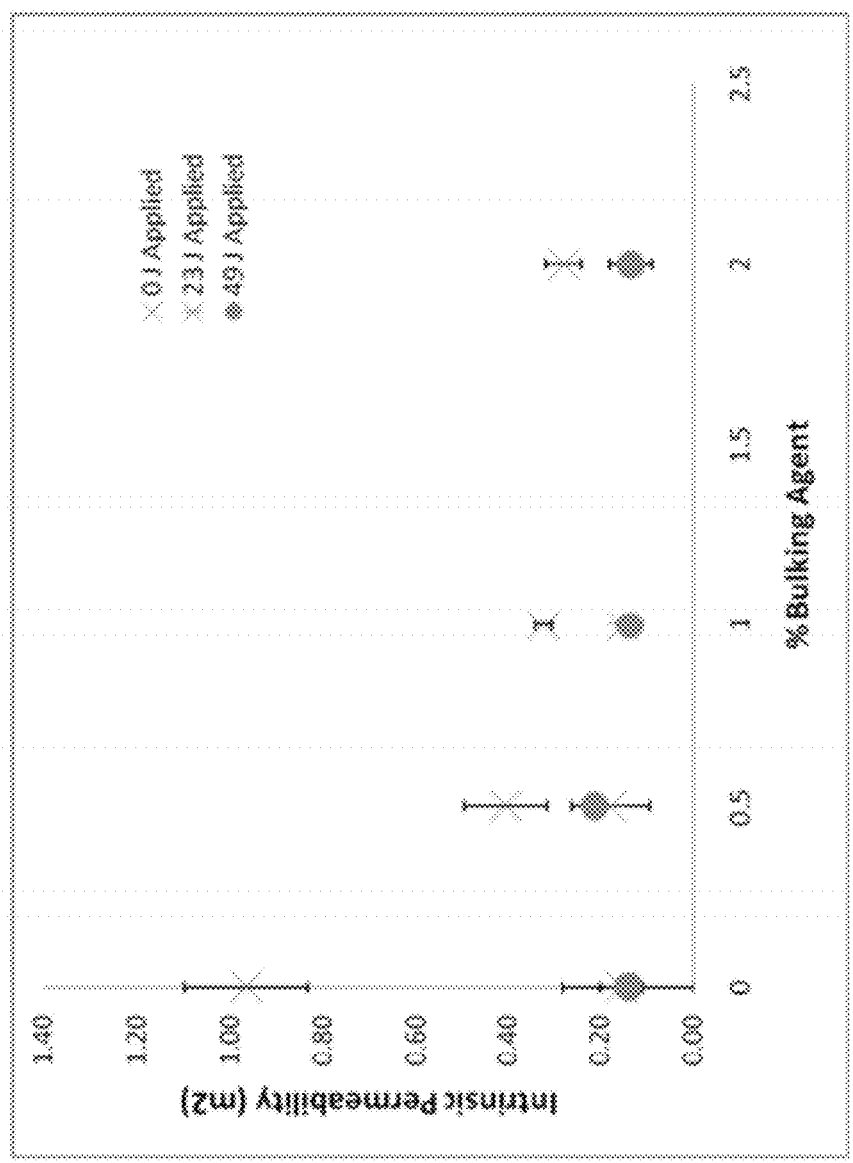
FIG. 7 shows the effect of wood chips and compression on intrinsic permeability in feed lot waste.

The same set of experiments were conducted with wood chips in addition to feedlot waste (FIG. 7). Addition of wood chips did not show the same benefits of straw in terms of increasing permeability of the waste when under compression. In addition the wood chips were added up to 2% of the total mass, while only 0.2% by mass of straw was required for observable differences in permeability under compression.

Another promising method of improving the porosity of low porosity/shear strength wastes is to separate the "problem" portions of the waste. In this method, the smallest particles from the substrates to be placed in the leachate bay reactor can be removed. These, small particles fall into air voids between larger particles and essentially clog the voids slowing the passage of water. These small particles are well suited to conventional anaerobic digestion due to the large relative surface area and low risk of forming floating mats on the digester surface.

Figure 8:
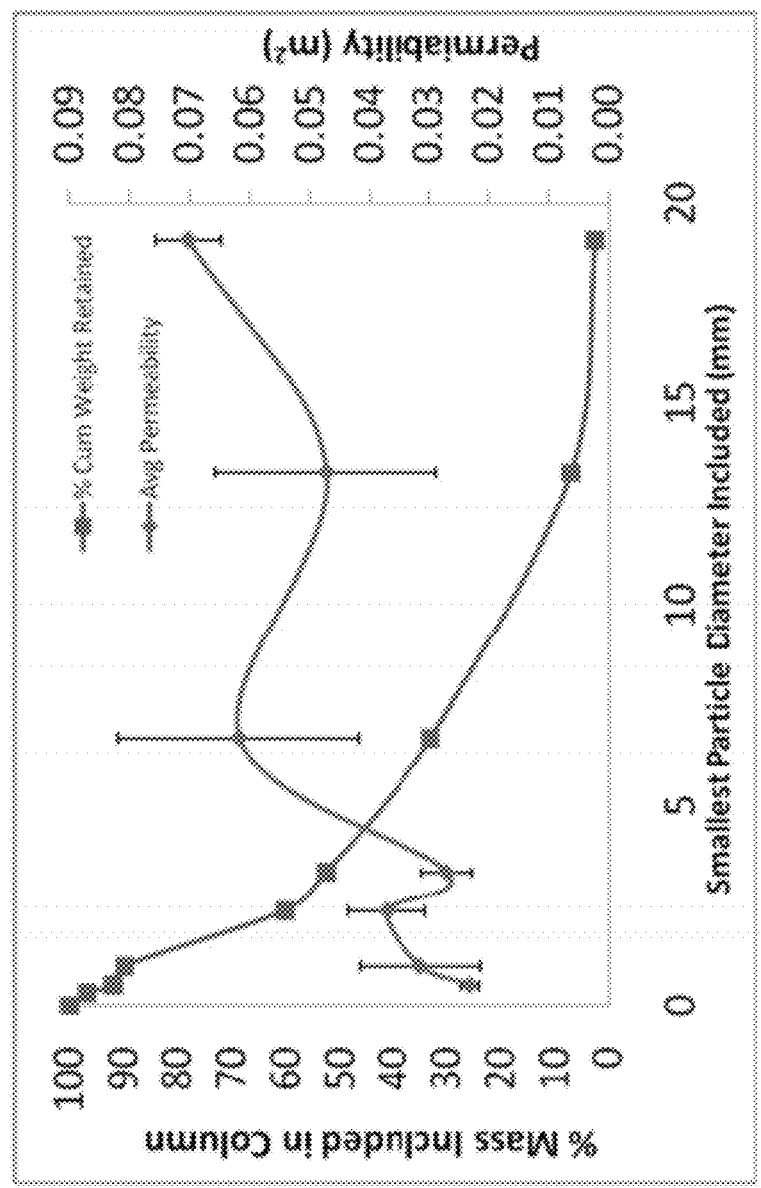
FIG. 8 shows the effect of exclusion of small particles in columns on Waste permeability.

FIG. 8 outlines the different permeability values of different size fractions of feedlot waste. A general trend of increasing permeability as smaller particles are excluded has been observed. In particular, a large increase in permeability is noted when particles smaller than 7 mm are excluded (FIG. 8). There is a large difference between exclusion of particles less than 3 mm and those less than 7 mm.

Based on the teachings herein, the exact threshold where increased permeability occurs can be readily determined with routine experimentation. It is possible that the small particles can still be anaerobically digested to produce methane in the systems and methods described herein, if sent directly to the leachate storage reactor.

The embodiments of the invention described herein are implemented as steps in one or more systems. The implementation is a matter of choice, dependent on the performance requirements of the system implementing the invention. Accordingly, the operations making up the embodiments of the invention described herein are referred to variously as operations or steps. Furthermore, it should be understood that operations may be performed in any order, unless explicitly claimed otherwise or a specific order is inherently necessitated by the claim language.

The above specification, examples, and data provide a complete description of the structure and use of exemplary embodiments of the invention. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. A method comprising:
    feeding waste streams of different solid content into one of a leachate bay reactor, a leachate storage tank, and a high rate reactor such that each of the leachate bay reactor, the leachate storage tank, and the high rate reactor receives waste stream with different values for at least one waste stream characteristic;
    recirculating leachate between the leachate bay reactor for hydrolysis and the leachate storage tank;
    cycling leachate from the leachate storage tank to the high rate reactor for methogenesis;
    and cyclically processing the waste streams in the leachate bay reactor through anaerobic and aerobic cycles.

2. The method of claim 1 wherein the at least one characteristic is the amount of solid content in the waste stream.

3. The method of claim 2 wherein the waste streams include a diluted waste stream with solid content between one percent and ten percent and a soluble waste stream with solid content below one percent.

4. The method of claim 3 wherein the diluted waste stream is fed to the leachate storage tank and the soluble waste stream is fed to the high rate reactor.

5. The method of claim 1 further comprising aerating to compost organic materials that are not readily degraded under anaerobic conditions.

6. The method of claim 1 further comprising using the anaerobic cycle to digest biodegradable compounds and the aerobic cycle to degrade organic compounds.

7. The method of claim 1 wherein processing the waste streams through an aerobic cycle comprises pumping air through the leachate bay reactor.

8. A digester comprising:
    a leachate bay reactor, wherein the leachate bay reactor is a transport container for waste;
    a leachate storage tank fluidically connected to the leachate bay reactor to recirculate leachate through the leachate bay reactor; and
    a high rate methanogenic reactor fluidically connected to the leachate storage tank to cycle the leachate in a high rate methanogenic reactor for biogas production, wherein, each of the leachate bay reactor, the leachate storage tank, and the high rate methanogenic reactor is used for processing waste streams with different values for at least one waste stream characteristic.

9. The digester of claim 8 wherein the at least one characteristic is the amount of solid content in the waste stream.

10. The digester of claim 8 wherein the waste streams include a diluted waste stream with solid content between one percent and ten percent and a soluble waste stream with solid content below one percent.

11. The digester of claim 8 wherein the type of waste fed to at least one of the leachate bay reactors, the leachate storage tank, and the high rate reactor depends at least to some extent on waste solids content.

12. The digester of claim 8 wherein the leachate storage tank is configured to hydrolyze organics from the waste streams.

13. The digester of claim 8 wherein the high rate methanogenic reactor produces biogas from solubilized organic matter.

14. The digester of claim 8 wherein the leachate storage tank facilitates acido/acetogensis.

15. A digester system comprising:
    a modular leachate bay reactor having a plurality of bays;
    a leachate storage tank to hydrolyze organics from waste streams; and
    a high rate methanogenic reactor to cycle the leachate from the leachate storage tank for biogas production and
    a three stage crystallizer having an auger assembly, hydrocyclone classifier, and gravity settling basin, the crystallizer producing struvite and separating the struvite from the leachate to reduce ammonium and phosphate accumulation in the leachate,
    wherein, each of the leachate bay reactor, the leachate storage tank, and the high rate methanogenic reactor is used for processing waste streams with different values for at least one waste stream characteristic.

16. The digester system of claim 15 further comprising a sacrificial high rate methanogenic reactor.

17. The digester of claim 15, wherein the waste streams include a diluted waste stream with solid content between one percent and ten percent and a soluble waste stream with solid content below one percent.

18. The digester of claim 17, wherein the diluted waste stream is fed to the leachate storage tank and the soluble waste stream is fed to the high rate reactor.

* * * * *